(12) United States Patent
Klotz et al.

(10) Patent No.: US 7,135,017 B2
(45) Date of Patent: *Nov. 14, 2006

(54) IMAGING AND SURGICAL PROCEDURE FOR CARPAL TUNNEL SYNDROME

(75) Inventors: Conrad Lee Klotz, Nappanee, IN (US); Sarah Elizabeth Stephens, North Webster, IN (US); Robert J. Dunki-Jacobs, Mason, OH (US); Inderraj S. Makin, Loveland, OH (US)

(73) Assignee: DePuy Products, Inc., Warsaw, IN (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/610,463

(22) Filed: Jun. 30, 2003

(65) Prior Publication Data

US 2004/0267253 A1 Dec. 30, 2004

(51) Int. Cl.
*A61B 18/18* (2006.01)
*A61B 8/00* (2006.01)

(52) U.S. Cl. .................. 606/28; 600/439; 600/471

(58) Field of Classification Search .................. 606/1, 606/27, 28, 41, 46, 170, 104, 439, 471
See application file for complete search history.

(56) References Cited

U.S. PATENT DOCUMENTS

| 4,509,524 A | 4/1985 | Miwa |
| 4,962,770 A * | 10/1990 | Agee et al. .................. 128/898 |
| 5,423,804 A * | 6/1995 | Kulick .......................... 606/14 |
| 5,458,130 A | 10/1995 | Kaufman et al. |
| 5,667,473 A * | 9/1997 | Finn et al. .................. 600/104 |
| 5,795,311 A | 8/1998 | Wess |
| 5,924,999 A | 7/1999 | Agee et al. |
| 5,954,675 A * | 9/1999 | Dellagatta ...................... 601/3 |
| 6,364,849 B1 | 4/2002 | Wilcox |
| 2004/0019303 A1* | 1/2004 | Thomson .................... 600/595 |

OTHER PUBLICATIONS

"SafeGuard—Mini Carpal Tunnel Release System", Kinetikos Medical Incorporated (KMI), Apr. 1999 (6 pages).

(Continued)

*Primary Examiner*—Michael Peffley
(74) *Attorney, Agent, or Firm*—Maginot, Moore & Beck

(57) ABSTRACT

A system, method and/or apparatus is provided for visualization or imaging of the transverse carpal ligament and surrounding structures/features of a hand of a patient, and treatment of the transverse carpal ligament, particularly, but not necessarily, for performing non-invasive carpal tunnel release. The subject invention utilizes ultrasound waves preferably, but not necessarily, in the high frequency range and cavitations to image the transverse carpal ligament (TCL), record its location in three-dimensional space, and perform precision treatment on the transverse carpal ligament. Treatment may range from stretching or lengthening the TCL to complete tissue ablation or dissection of a portion or portions of the TCL (as is performed in a standard carpal tunnel release procedure) in order to release pressure within the carpal tunnel. Particularly, high temperature conditions are generated at target tissue of the TCL resulting in elongation or necrosis/dissection. The subject system, apparatus and/or method provides the surgeon to relieve a patient of carpal tunnel syndrome symptoms in a bloodless, efficient, and accurate manner.

10 Claims, 7 Drawing Sheets

OTHER PUBLICATIONS

Viegas, Steven F. et al., "Extra-Bursal Technique of Endoscopic Release of the Carpal Ligament", An Illustrated Guide to the Modified Chow Technique Endoscopic Release of the Carpal Ligament, Smith & Nephew, Inc., Nov. 14, 1997 (12 pages).

"Unparalleled Performance Inside and Out", Dec. 2002, Koninklijke Philips Electronics N.V., (16 pages).

"Case Studies—SonoCT™ Real-time Compound Imaging", Jun. 2001, Agilent Technologies Healthcare Solutions Group (2 pages).

"Comparison of Image Clarity—SonoCT™ Real-time Compound Imaging Versus Conventional 2D Ultrasound Imaging", Agilent Technologies Healthcare Solutions Group, Jun. 2001 (12 pages).

* cited by examiner

IMAGING AND SURGICAL PROCEDURE FOR CARPAL TUNNEL SYNDROME

CROSS-REFERENCE TO RELATED APPLICATIONS

Cross-reference is hereby made to related co-pending U.S. patent application Ser. No. 10/610,474 filed on Jun. 30, 2003.

BACKGROUND

1. Field of the Invention

The present invention relates to procedures for relieving problems associated with carpal tunnel syndrome and, more particularly, to a procedure for performing a minimally invasive to non-invasive surgical procedure on a transverse carpal ligament.

2. Background Information

Carpal tunnel syndrome is a common problem that affects the hand and wrist. This condition, or syndrome, has become the focus of much attention in the last few years due to suggestions that it may be linked to certain occupations that require repetitive use of the hands, such as typing. While certain occupations may experience more problems with carpal tunnel syndrome, many people develop this condition regardless of their occupation.

Particularly, carpal tunnel syndrome (CTS) is a condition that results when the median nerve of the hand does not function properly. Usually, this occurs because there is too much pressure on the median nerve that extends into the wrist through an opening called the carpal tunnel. The median nerve extends into the hand to receive sensation from the thumb, index finger, long finger, and half of the ring finger. The median nerve also provides a branch to the muscles of the thumb (i.e. the thenar muscles).

The carpal tunnel is an opening into the hand that is made up of the bones of the wrist (i.e. the carpals) on the bottom and the transverse carpal ligament on the top. The median nerve and the flexor tendons extend through the carpal tunnel into the hand. The median nerve lies just under the transverse carpal ligament. A material called the tenosynovium covers the flexor tendons. The tenosynovium is slippery and thus allows the tendons to glide against each other as they move. Any condition that causes irritation or inflammation of the tendons can result in swelling and/or thickening of the tenosynovium. As the tenosynovium begins to swell and/or thicken, pressure begins to increase in the carpal tunnel. This is because the bones and ligaments that constitute the carpel tunnel are fixed in size and thus are not able to stretch in response to the swelling. Increased pressure in the carpel tunnel begins to squeeze the median nerve against the transverse carpal ligament, since the median nerve is the softest structure in the carpal tunnel. Eventually, the pressure reaches a point where the median nerve can no longer function normally. This manifests itself as pain and numbness in the hand.

There are many conditions that can result in irritation and inflammation of the tenosynovium, and eventually cause carpal tunnel syndrome. Different types of arthritis can cause inflammation of the tenosynovium directly. A fracture of the wrist bones may later cause carpal tunnel syndrome if the healed fragments result in abnormal irritation on the flexor tendons. Particularly, anything that causes abnormal pressure on the median nerve will result in the symptoms of carpal tunnel syndrome.

In the early stages of carpal tunnel syndrome, non-operative treatments are typically used. One such non-operative treatment is the use of a brace. The brace keeps the wrist in a neutral position. When the wrist is in a neutral position, the carpal tunnel is as large as it can be so the median nerve has as much room as possible.

Another non-operative treatment that tries to reduce the symptoms of carpal tunnel syndrome is the use of anti-inflammatory medications to help control swelling of the tenosynovium. Anti-inflammatory medications include over the counter medications such as ibuprofen and aspirin, as well as high doses of vitamin B-6. Injections of cortisone into the carpal tunnel may also be used in order to decrease swelling of the tenosynovium and thereby give temporary relief of symptoms.

If the non-operative treatments fail to control the symptoms of carpal tunnel syndrome, surgery may be required to reduce the pressure on the median nerve. There are essentially three surgical techniques designed to relieve pressure on the median nerve. The first and most common surgical procedure is the traditional open incision technique. The second surgical procedure is known as the mini-open. The third procedure is an endoscopic technique.

The traditional open incision technique requires a 2 to 2½ inch incision to be made in the palm of the hand. A structure called the palmer fascia is then incised in order to reach the transverse carpal ligament. The transverse carpal ligament is then cut while making sure that the median nerve is out of the way and protected. The cut or incision may be slight (small incised amount) or drastic (e.g. as in a full carpal tunnel release (CTR) procedure). Pressure on the median nerve is relieved after cutting of the transverse carpal ligament. The incised skin is then sutured. The transverse carpal ligament remains open and the gap is slowly filled by scar tissue.

Major drawbacks to the standard, open incision technique are the slowness of recovery and the size of the resulting scar. Often the 2 inch palm side scar remains sensitive to direct pressure for approximately six to eight weeks. For a working patient, this scar sensitivity can preclude return to normal work activities. In summation, the greater the invasiveness, the longer patient recovery time.

The mini-open technique utilizes a 1 to 1½ cm incision proximate the transverse carpal ligament. Various instruments are placed through the incision and utilized to cut the TCL from underneath as appropriate.

In the endoscopic carpal tunnel release technique, a small horizontal incision is made at the wrist and an arthroscope is introduced underneath the transverse carpal ligament. A small knife or blade, attached to the end of the arthroscope, is utilized to incise or cut the transverse carpal ligament. Again, cutting through the transverse carpal ligament alleviates the compression on the median nerve. While the endoscopic carpal tunnel release technique is less invasive than the traditional, and is typically accomplished on an outpatient basis, it is nonetheless an invasive procedure that requires time to heal. With the endoscopic method, however, poor or low quality visualization typically tends to make surgeons prefer an open technique.

Moreover, with current invasive techniques, the surgeon must rely on his/her own expertise for visualization, not only for the initial incision on the palm of the hand, but also in locating where dissection of the transverse carpel ligament takes place. The place of dissection is critical because while it is desired to split the transverse carpal ligament, the surgeon must not lacerate any major branch of the median or ulnar nerves.

Furthermore, although current complication rates are low (approximately 3–4%), inadvertent laceration of a nerve (either fully or partially) can have catastrophic effects on the functionality of the patient's hand, as well as impact the surgeon's practice. Because of the risks, may patients suffering from carpal tunnel syndrome forego the surgical procedure because of the involved risks.

It should be appreciated in view of the above, that it is desired to have a non-invasive technique for performing carpal tunnel release.

It should also be appreciated in view of the above, that it is desired to have pre-surgical visualization of all critical structures (e.g. nerves, blood vessels, transverse carpal ligament, etc.) particularly in order to produce more accurate work and/or reduce surgical mistakes.

SUMMARY

The subject invention is a system, method and/or apparatus for minimally invasive to non-invasive surgical treatment of carpal tunnel syndrome. Particularly, the subject invention is a system, method and/or apparatus for performing a minimally invasive to non-invasive transverse carpal ligament treatment procedure.

According to an aspect of the subject invention, three-dimensional imaging is obtained of structures and/or features of a patient's wrist, particularly internal tissue and/or with respect to bone structure(s) of the wrist utilizing an imager. The three-dimensional imaging is stored and/or utilized to provide targeted treatment for and/or on the transverse carpal ligament particularly, but not exclusively, for performing a carpal tunnel release. This allows the surgeon to register the location of critical structures within the patient's wrist/hand. Once appropriate inputs have been made and a plan of treatment confirmed, treatment of the transverse carpal ligament may be commenced in accordance with another aspect of the subject invention. The imaging and/or treatment may be performed in a non-invasive manner (i.e. without an incision), in a minimally invasive manner (i.e. with a small incision), or even in a fully invasive manner (i.e. with a small to large incision); the non-invasive or minimally invasive manner being preferred. The imager may use any one of a variety of emanations (signals, transmissions, emissions and/or the like).

In one form, the three-dimensional imaging locates the transverse carpal ligament particularly with respect to or additionally with the median nerve and/or its branches, carpals, carpal tunnel and/or the like in a patient's hand through the use of ultrasound, preferably, but not necessarily, high frequency ultrasound typically in the 7.5–30 MHz range. The location of the transverse carpal ligament is then utilized for commencement of surgical treatment of the transverse carpal ligament ranging from a full carpal tunnel release to a mere cutting or necrosis of a portion of the TCL as well as stretching a portion or all of the TCL.

According to another aspect of the subject invention, a surgical procedure on the transverse carpal ligament is provided. Particularly, a high temperature condition is generated at or on a target area or areas of the transverse carpal ligament. The high temperature condition causes elongation or stretching of the target area(s) of the transverse carpal ligament, or necrosis, ablation and/or dissection of the area(s) of the transverse carpal ligament. The high temperature condition is preferably, but not necessarily, generated by application of ultrasound, preferably in the high frequency ultrasound range.

In one particular form, the subject invention provides a method of performing treatment on a transverse carpal ligament of a wrist of a patient. The method includes the steps of: (a) locating the transverse carpal ligament relative to internal structures proximate the transverse carpal ligament; (b) determining a plan of treatment for the transverse carpal ligament; and (c) creating a high temperature condition at a target area of the transverse carpal ligament to provide the determined plan of treatment.

In another particular form, the subject invention provides a system for performing treatment of the transverse carpal ligament. The system includes: (a) an imager configured to obtain a three-dimensional image of a transverse carpal ligament of a wrist of a patient relative to internal structures of the wrist proximate the transverse carpal ligament; (b) a signal generator configured to generate signals operative to produce an elevated temperature in targeted tissue; and (c) an applicator in communication with the generator and configured to apply the generated signals to a selected target tissue area of the transverse carpal ligament according to the obtained three-dimensional image.

The subject invention provides the benefits of: i) providing a minimally invasive to non-invasive, bloodless and relatively painless surgical procedure; ii) providing a greater degree of visualization; and iii) providing a decrease in risk to patients and a decrease in liability to physicians.

BRIEF DESCRIPTION OF THE DRAWINGS

In the drawings.

Corresponding reference characters indicate corresponding parts throughout the several views. Like reference characters tend to indicate like parts throughout the several views.

DESCRIPTION OF THE PREFERRED EMBODIMENT(S)

Figure 1:
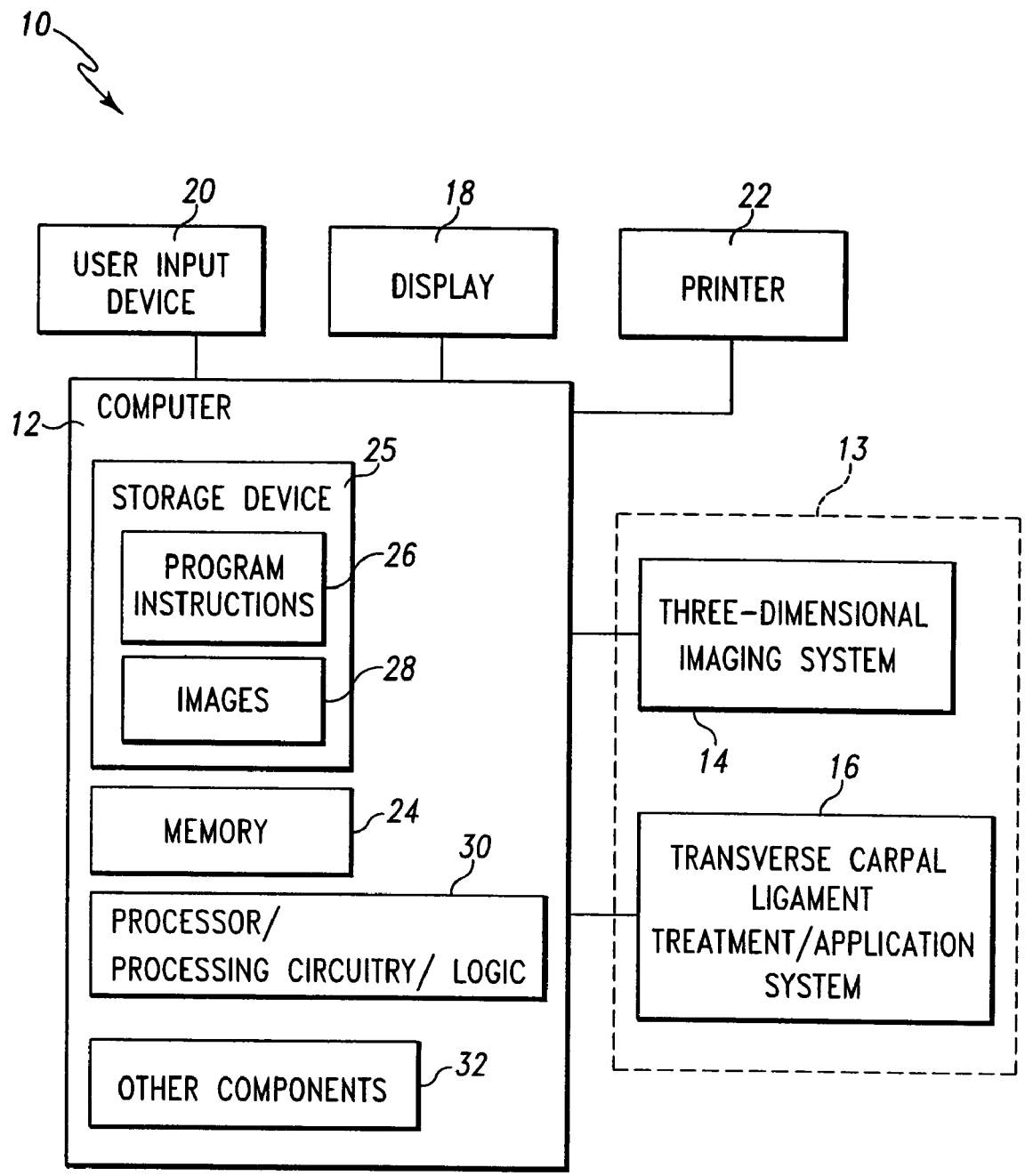
FIG. 1 is a block diagram of a non-invasive treatment system for carpal tunnel problems in accordance with the principles of the subject invention.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

Referring now to FIG. 1 there is shown a block diagram of an exemplary system, generally designated 10, for three-dimensional (3-D) imaging of a transverse carpal ligament of a wrist of a hand and providing treatment (preferably, but not necessarily in a non-invasive manner) to the wrist area of a patient, particularly the transverse carpal ligament such as for relieving carpal tunnel syndrome and/or its symptoms. The system 10 provides for the three-dimensional imaging and the recording of the location of at least the transverse carpal ligament and preferably, the transverse carpal ligament and surrounding structures or features of a patient's wrist. The system 10 also provides for treatment to the transverse carpal ligament that is preferably, but not necessarily, based on the 3-D imaging thereof. The treatment ranges from stretching or elongation of a target area or target areas of the transverse carpal ligament to complete tissue ablation, necrosis and/or dissection of the transverse carpet ligament.

The system 10 produces an elevated temperature condition at a target area of a particular tissue or tissue type. This may be accomplished in a non-invasive manner or in a minimally invasive manner. It should be appreciated that while the subject invention is applicable for use in both non-invasive and minimally invasive manners, the subject invention is preferably used in a non-invasive manner. Therefore while hereinafter the term non-invasive is used with respect to the subject invention, invasive manners are covered as well. The elevated temperature condition is produced by energy waves particularly pressure waves, such as ultrasound. The pressure wave may be shaped as appropriate for the target area.

The system 10 may be used for performing a non-invasive carpal tunnel release procedure on the target area(s) of the transverse carpal ligament, typically for alleviating problems and/or symptoms associated with carpal tunnel syndrome, or a lesser procedure on the transverse carpal ligament. In this manner, the pressure within the carpal tunnel or canal is relieved in a bloodless, efficient and accurate manner. It should be appreciated that while the system will be described with respect to the transverse carpal ligament and/or wrist area, particularly for carpal tunnel release, the subject invention may be used for other tissue types and/or tissue areas.

The system 10 includes a computer, processing device, or other similar device 12 such as is known in the art. The computer 12 has a storage device 25, such as a hard drive, that stores program instructions 26 for the operation of the computer and for the operation, features and/or functionality of the subject invention as well as the functionality of the various components of the computer 12 and the various components of the system 10 as herein provided. As discussed below, the storage device 25 also stores still images and video (images) 28 as acquired and includes 3-D modeling and imaging software, treatment software, diagnostic software, interface software, and the like. The storage device 25 is operative to store, receive and allow deletion therefrom of various types of data. Memory 24 is also provided such as RAM for temporarily storing data and program instructions for execution and/or ROM for permanently storing data such as is known in the art.

A user input device such as a keyboard and/or mouse 20 is operatively connected to the computer 12. The user input device 20 is operative to accept or receive input from a user for operation of the subject invention. A display 18 is also coupled or connected to the computer 12 and is adapted to display images/video (including program interfaces, e.g. GUIs) thereon as received from the computer 12. Optionally, a printer 22 is operatively coupled or connected to the computer 12. If provided, the printer 22 is preferably a high resolution printer. The printer 22 is adapted to receive and print images, text and/or the like as necessary.

The computer 12 also includes a processor and/or processing circuitry/logic 30 that is operative, adapted and/or configured to utilize the program instructions 26 and/or control the various components of the computer 12 and/or the system 10. Other components of the computer 12 not described herein but which are typically part of a computer such as communication hardware, display adaptors, and/or the like are represented by the other components box 32.

In accordance with an aspect of the subject invention, the system includes an imaging and treatment portion, section, sub-system, or the like, generally designated 13. The imaging and treatment portion 13 may be separate from the computer 12 or may be at least partially integral with the computer 12 as represented by the dashed lines. In either case, the functioning is the same. The imaging and treatment portion 13 is configured, adapted and/or operative to perform three-dimensional tissue imaging, both static and dynamic, such as a transverse carpal ligament and surrounding structures/features, and provide treatment to a target area of the imaged tissue. The imaging and treatment portion also obtains data that is formed into the three-dimensional image. The obtained image is preferably stored in the images section 28 of the storage device 25.

Particularly, the imaging and treatment portion 13 includes a three-dimensional imaging system 14 and a tissue (transverse carpal ligament) treatment system 16. The imaging portion 14 obtains tissue images while the treatment/application portion 16 provides a non-invasive procedure that induces, generates, creates or produces an elevated temperature condition at the target tissue area preferably, but not necessarily, in accordance with the imaging, and at least with respect to a determined plan of treatment typically selected with regard to the imaging. The elevated temperature condition is localized heating of the target tissue area to a point where the target tissue is stretched or elongated, tissue ablation occurs at the target tissue area, tissue necrosis, tissue dissection, or other appropriate treatment effect on the tissue. The system 13 can provide intervals of imaging and treatment until a desired outcome is produced.

Figure 2:
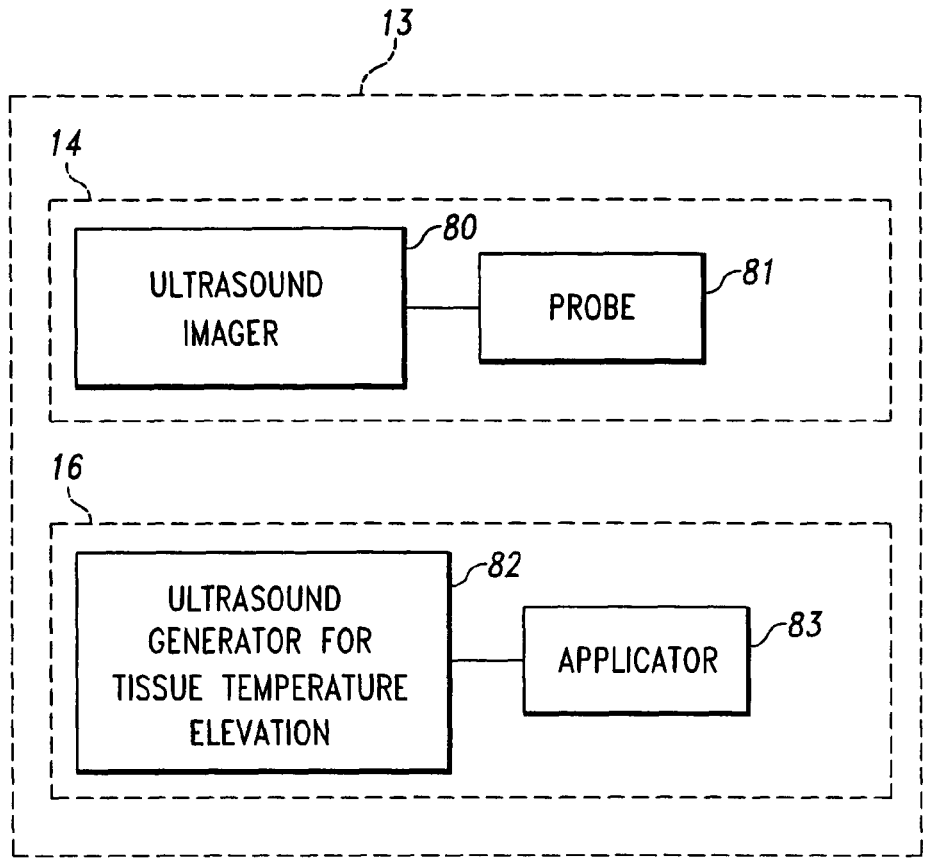
FIG. 2 is a block diagram of an exemplary embodiment of an imaging and treatment portion of the non-invasive treatment system of FIG. 1.

In FIG. 2 there is depicted a block diagram of an exemplary embodiment of the imaging and treatment portion 13 of the non-invasive diagnostic and treatment system 10 of FIG. 1. The imaging portion 14 is shown as including an ultrasound imager 80 and a probe 81 connected thereto. The treatment portion 16 is shown as including an ultrasound generator 82 and an applicator 83 connected thereto. It should be appreciated, however, that other imaging systems or imagers may be used much as MRIs, CAT scans, and/or the like.

The imaging portion 14 is operatively coupled or connected to the computer 12. The ultrasound imager 80 is configured, adapted and/or operative to cause the production or generation of ultrasound waves at a particular ultrasound frequency or at one or more of a plurality of ultrasound frequencies. The ultrasound imager 80 preferably is operative to controllably cause the production or generation of ultrasound in a frequency range of about 1.0 MHz to 35 MHz. Typically, low frequency ultrasound in the 1.0 to 7.5 MHz range is used for diagnostics/imaging and ultrasound of higher frequencies (from 7.5 MHz up to 35 MHz) for treatment as described herein.

An ultrasound probe 81 is operatively coupled or connected to the ultrasound imager 80. The probe 81 is adapted, configured and/or operative to produce, generate and/or emit the ultrasound waves in accordance with the ultrasound imager 80. The probe 81 thus serves as a source for ultrasound waves or signals. The probe 81 is also adapted, configured and/or operative to receive the ultrasound signals/waves that are reflected from or echo off of the internal wrist structures (tissues) and convert the received reflected ultrasound signals/waves into electrical signals. The received ultrasound signals/waves, being converted into electrical signals, are received by the ultrasound imager 80 to produce a reflected pattern. The reflected pattern is utilized by appropriate program instructions 26 to produce an image.

The probe 81 may be moved to provide three-dimensional imaging of the internal wrist structures including the transverse carpal ligament and location with respect to the other internal wrist structures. The probe 81 may be designed to be situated about the wrist such that various angles of ultrasound signals are produced and reflections received that provide a three-dimensional image of the wrist structures, particularly the transverse carpal ligament, carpal tunnel, and other adjacent structures.

While the ultrasound imager 80 is shown as a separate component, it should be appreciated that part or all of the ultrasound imager and/or its functionality may be incorporated into or as part of the computer 12 and/or its various components. In this case, the probe 81 may be directly coupled to the computer 12.

The treatment portion 16 is operatively coupled or connected to the computer 12. The treatment portion 16 is configured, adapted and/or operative to cause the production or generation of ultrasound waves or signals capable of providing heating of internal tissue at a target area. The treatment portion 16 includes an ultrasound generator 82 capable of providing high-frequency ultrasound waves for tissue temperature elevation at a tissue target area. An applicator 83 is operatively coupled or connected to the ultrasound generator 82. The applicator 83 is adapted, configured and/or operative to produce, generate and/or emit the ultrasound waves in accordance with the ultrasound generator 82. The applicator 83 thus serves as a source for the treatment ultrasound waves or signals.

The applicator 83 may be moved to provide treatment to a specific target area or target areas (collectively, target area) of the particular tissue undergoing treatment. The applicator 83 may be designed to be situated about the wrist such that various angles of ultrasound treatment signals are produced, particularly for treatment of the transverse carpal ligament.

While the ultrasound generator 82 is shown as a separate component, it should be appreciated that part or all of the ultrasound generator and/or its functionality may be incorporated into or as part of the computer 12 and/or its various components. In this case, the applicator 83 may be directly coupled to the computer 12.

Figure 3:
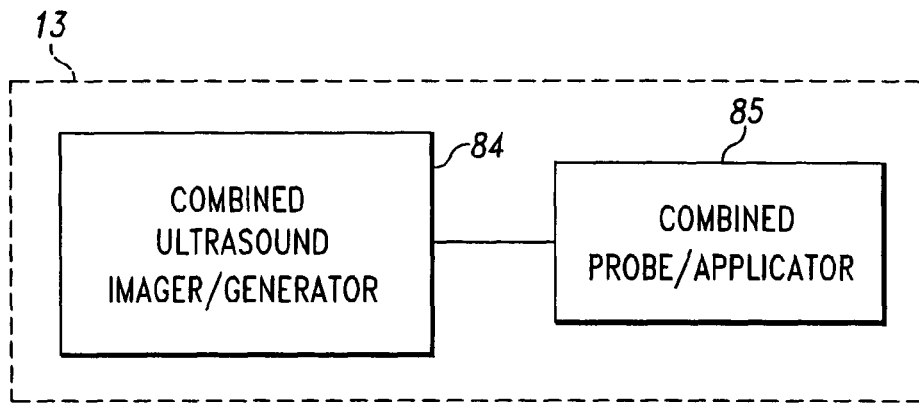
FIG. 3 is a block diagram of another exemplary embodiment of an imaging and treatment portion of the non-invasive treatment system of FIG. 1.

Referring to FIG. 3, there is depicted a block diagram of another exemplary embodiment of the imaging and treatment portion 13. In this embodiment, a combined ultrasound imager and generator 84 substitutes for the separate ultrasound imager 14 and the ultrasound generator 82 of FIG. 2. The combined ultrasound imager/generator 84 is configured, operative and/or adapted to perform in the same manner as described above for the separate components. Moreover, the imaging and treatment portion 13 includes a combined probe/applicator 85 that likewise, combines the functionality of the probe 81 and applicator 83 of FIG. 2 into a single unit.

It should be appreciated that while the ultrasound imager/generator 84 is shown as a separate component, it should be appreciated that part or all of the ultrasound imager/generator and/or its functionality may be incorporated into or as part of the computer 12 and/or its various components. In this case, the probe/applicator 85 may be directly coupled to the computer 12.

Figure 4:
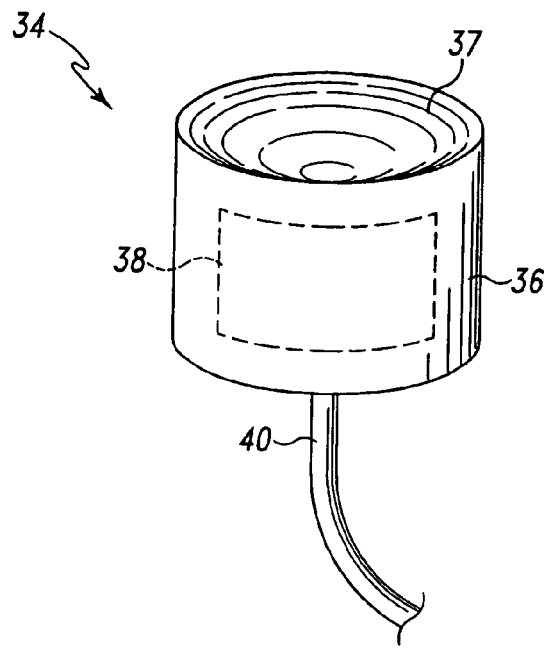
FIG. 4 is a perspective view of an exemplary configuration of a combined probe/applicator for imaging a transverse carpal ligament and surrounding structures of the wrist and/or treatment thereof in accordance with the present principles.

Referring now to FIG. 4, there is depicted an exemplary embodiment of a probe and/or treatment/applicator device generally designated 34. The probe/treatment (or probe/applicator) device 34 is an exemplary embodiment of one of the probe 81, the applicator 83, or the combined probe/applicator 85 (collectively hereinafter, probe/applicator device). The probe/applicator device 34 is operative, adapted and/or configured to produce and emit ultrasound waves and receive reflected ultrasound waves. The probe/applicator device 34 has a body or shell 36 that is formed as an essentially large diameter, small (axial) length cylinder having an essentially round head 37. The head 37 is utilized to abut or be in contact with the skin, typically via a transmission jelly such as in known in the art. As such, the head 37 is shaped accordingly to take into account the typical shape of a wrist.

The body 36 houses a transducer 38 such as a crystal. The transducer 38 is operative to produce and emit ultrasound waves of the appropriate frequency and receive (capture) reflected ultrasound waves. The transducer 38 converts the captured ultrasound waves into electrical signals that are transmitted via conductor 40 to the ultrasound imaging device/generator 14 and/or the computer 12.

While depicted as a single device, the transducer 38 may be two separate devices. One device would be the ultrasound source, while the other device would be the ultrasound receiver. The source device may constitute a single transducer or an array of transducers for three-dimensional imaging. The receiver device likewise may be a single transducer of an array of transducers. Moreover, the housing 36 is sized to be positioned over and/or around the wrist of a patient.

Figure 5:
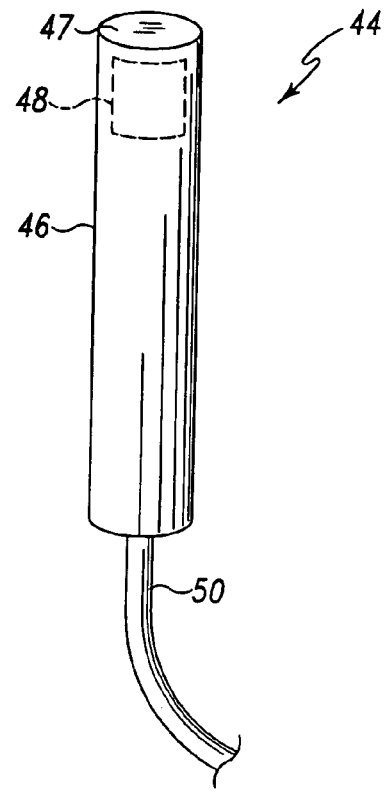
FIG. 5 is a perspective view of another exemplary configuration of a combined probe/applicator for imaging a transverse carpal ligament and surrounding structures of the wrist and/or treatment thereof in accordance with the present principles.

Referring now to FIG. 5, there is depicted another exemplary embodiment of a probe and/or treatment/applicator device generally designated 44. The probe/treatment (or probe/applicator) device 44 is an exemplary embodiment of one of the probe 81, the applicator 83, or the combined probe/applicator 85 (collectively hereinafter, probe/applicator device). The probe/applicator device 44 is operative, adapted and/or configured to produce and emit ultrasound waves and receive reflected ultrasound waves. The probe/applicator device 44 has a body or shell 46 that is formed as an essentially small diameter, large (axial) length cylinder having an essentially round head 47. The head 47 is utilized to abut or be in contact with the skin, typically via a transmission jelly such as in known in the art. As such, the head 47 is shaped accordingly to take into account the typical shape of a wrist.

The body 46 houses a transducer 48 such as a crystal. The transducer 48 is operative to produce and emit ultrasound waves of the appropriate frequency and receive (capture) reflected ultrasound waves. The transducer 48 converts the captured ultrasound waves into electrical signals that are transmitted via conductor 50 to the ultrasound imaging device/generator 14 and/or the computer 12.

While depicted as a single device, the transducer 48 may be two separate devices. One device would be the ultrasound source, while the other device would be the ultrasound receiver. The source device may constitute a single transducer or an array of transducers for three-dimensional imaging. The receiver device likewise may be a single transducer of an array of transducers. Moreover, the housing 46 is sized to be positioned over and/or around the wrist of a patient.

Figure 6:
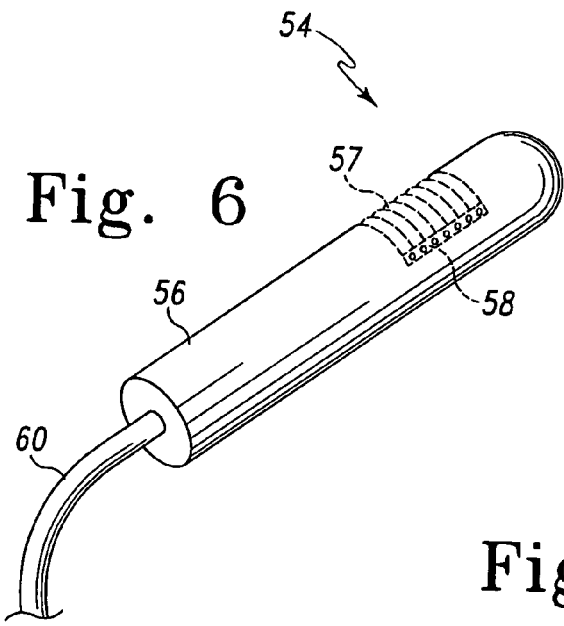
FIG. 6 is a perspective view of yet another exemplary configuration of a combined probe/applicator for imaging a transverse carpal ligament and surrounding structures of the wrist and/or treatment thereof in accordance with the present principles.

Referring now to FIG. 6, there is depicted yet another exemplary embodiment of a probe and/or treatment/applicator device generally designated 54. The probe/treatment (or probe/applicator) device 54 is an exemplary embodiment of one of the probe 81, the applicator 83, or the combined probe/applicator 85 (collectively hereinafter, probe/applicator device. The probe/applicator device 54 is operative, adapted and/or configured to produce and emit ultrasound waves and receive reflected ultrasound waves. The probe/applicator device 54 has a body or shell 56 that is formed as an elongated wand. The wand 56 has a transmission/reception area 57 that is shaped to contact the wrist area of the hand of the patient.

The body 46 houses a transducer 48 such as a crystal. The transducer 48 is operative to produce and emit ultrasound waves of the appropriate frequency and receive (capture) reflected ultrasound waves. The transducer 48 converts the captured ultrasound waves into electrical signals that are transmitted via conductor 40 to the ultrasound imaging device/generator 14 and/or the computer 12.

While depicted as a single device, the transducer 48 may be two separate devices. One device would be the ultrasound source, while the other device would be the ultrasound receiver. The source device may constitute a single transducer or an array of transducers for three-dimensional imaging. The receiver device likewise may be a single transducer of an array of transducers.

Figure 7:
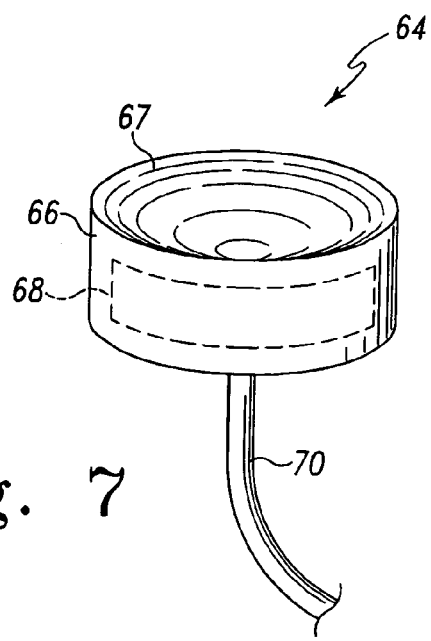
FIG. 7 is a perspective view of still another exemplary configuration of a combined probe/applicator for imaging a transverse carpal ligament and surrounding structures of the wrist and/or treatment thereof in accordance with the present principles.

Referring now to FIG. 7, there is depicted another exemplary embodiment of a probe and/or treatment/applicator device generally designated 64. The probe/treatment (or probe/applicator) device 64 is an exemplary embodiment of one of the probe 81, the applicator 83, or the combined probe/applicator 85 (collectively hereinafter, probe/applicator device). The probe/applicator device 64 is operative, adapted and/or configured to produce and emit ultrasound waves and receive reflected ultrasound waves. The probe/applicator device 64 has a body or shell 66 that is formed as an essentially large diameter, small (axial) length cylinder having an essentially oval and/or curved head 67. The head 67 is utilized to abut or be in contact with the skin and be around at least 180° around the wrist, typically via a transmission jelly such as in known in the art. As such, the head 67 is shaped accordingly to take into account the typical shape of a wrist.

The body 66 houses a transducer 68 such as a crystal. The transducer 48 is operative to produce and emit ultrasound waves of the appropriate frequency and receive (capture) reflected ultrasound waves. The transducer 48 converts the captured ultrasound waves into electrical signals that are transmitted via conductor 50 to the ultrasound imaging device/generator 14 and/or the computer 12.

While depicted as a single device, the transducer 48 may be two separate devices. One device would be the ultrasound source, while the other device would be the ultrasound receiver. The source device may constitute a single transducer or an array of transducers for three-dimensional imaging. The receiver device likewise may be a single transducer of an array of transducers. Moreover, the housing 46 is sized to be positioned over and/or around the wrist of a patient.

Figure 8:
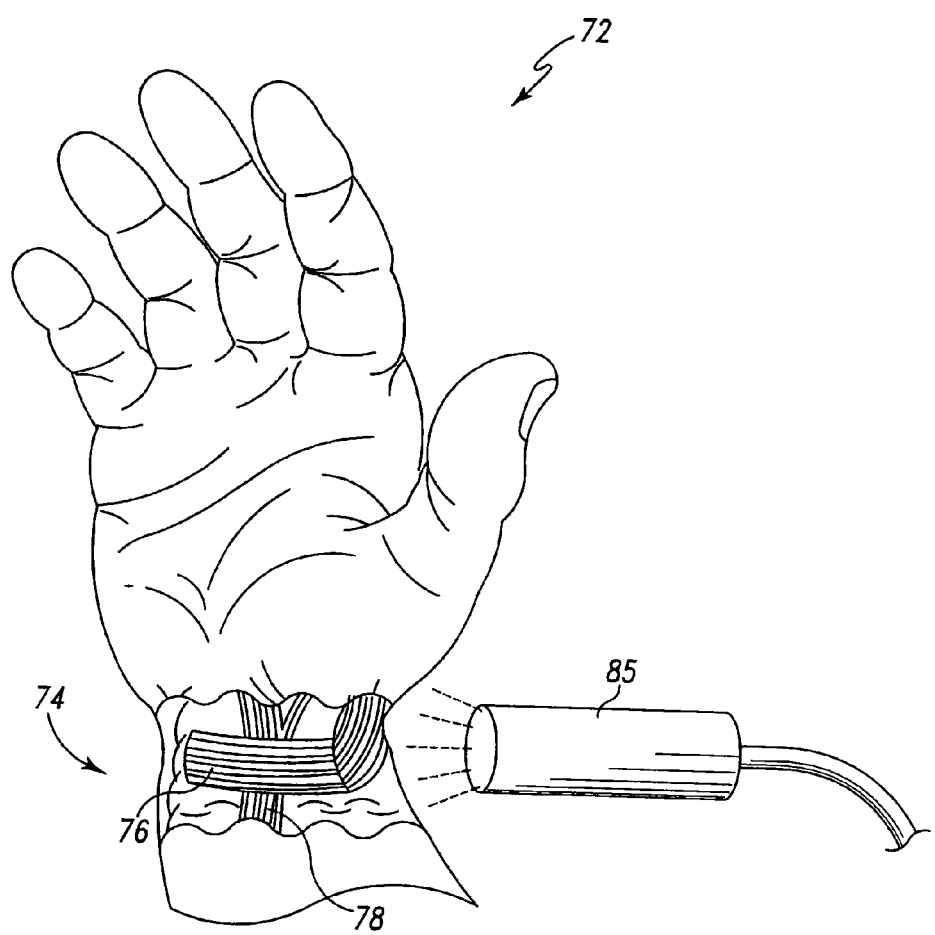
FIG. 8 is an illustration of an imaged wrist of a hand of a patient receiving treatment in accordance with the present principles.

In FIG. 8, there is depicted a hand 72 of a patient in order to illustrate an exemplary manner of utilizing the system 10 and of an exemplary manner of performing a non-intrusive carpal tunnel release. The wrist area 74 of the hand 72 has been imaged in 3-D, particularly the transverse carpal ligament 76, by a combined probe/applicator 85. The transverse carpal ligament 76 is shown in relation to the median nerve 78. The 3-D imaging is preferably stored and used in determining an appropriate treatment for the transverse carpal ligament 76. The transverse carpal ligament 76 is also located with respect to other features or structures of the wrist 74 that are not shown.

The probe/applicator 84 is providing preferably high-frequency ultrasound treatment to a selected or particular target area or areas of the transverse carpal ligament. Depending on the frequency and/or length of time of exposure, the target area tissue will be elongated (stretched), ablated, dissected, or be subject to necrosis. Of course, other probe shapes may be utilized.

Figure 9:
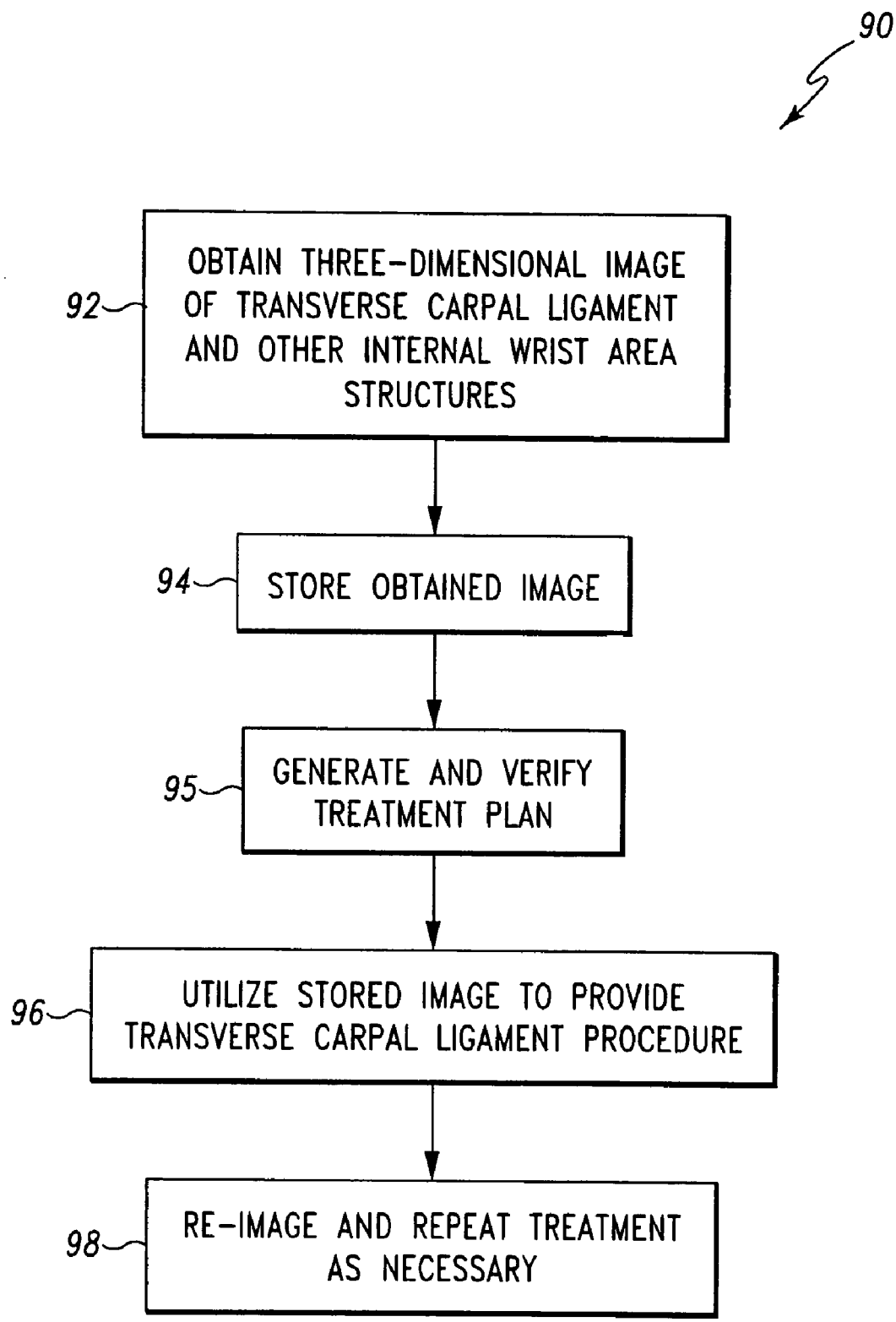
FIG. 9 is a flowchart of an exemplary carpal tunnel release procedure in accordance with the present principles.

Referring now to FIG. 9, there is depicted a flowchart, generally designated 90, of an exemplary manner of performing a non-intrusive carpal ligament release in accordance with the present principles and preferably, but not necessarily, using the present system 10. In step or block 92, a three-dimensional image of a transverse carpal ligament and other internal wrist structures is obtained. In step 94, the obtained three-dimensional image is stored. In step 96, the stored three-dimensional image is utilized to provide a non-invasive carpal tunnel release (CTR) procedure. The procedure of step 96 may entail a complete treatment, or may entail a partial treatment. For a partial treatment, after a first treatment, the transverse carpal ligament may be re-imaged and treatment is repeated. The repeated treatment may be to the same target area or to a different target area.

Figure 9A:
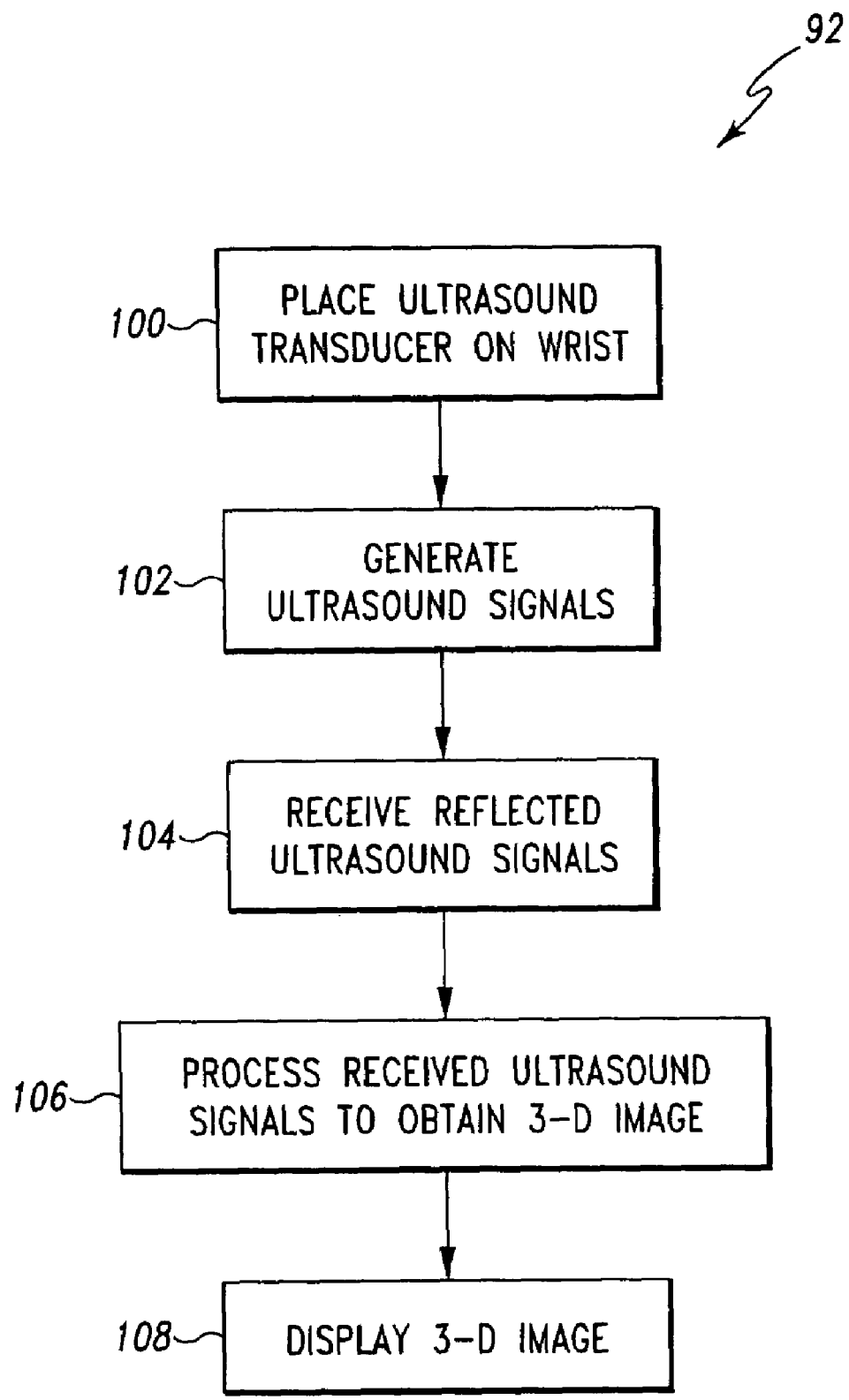
FIG. 9A is a flowchart of an exemplary manner of carrying out a step of the flowchart of FIG. 9.

In FIG. 9A, an expanded flowchart of step 92 is shown. It should be appreciated that the expanded flowchart of step 92 is only exemplary of a manner of executing step 92. In step 100, an ultrasound transducer is placed on the wrist of a patient. In step 102, ultrasound signals are generated that are transmitted into the wrist area. In step 104, ultrasound signals that are reflected by the underlying tissue/tissue structures (including the transverse carpal ligament and the median nerve) are received by the probe. The signals, in step 106, are processed to obtain a three-dimensional image of the transverse carpal ligament and it relationship to the other structures of the wrist. Optionally, in step 108, the generated three-dimensional image is displayed.

Figure 9B:
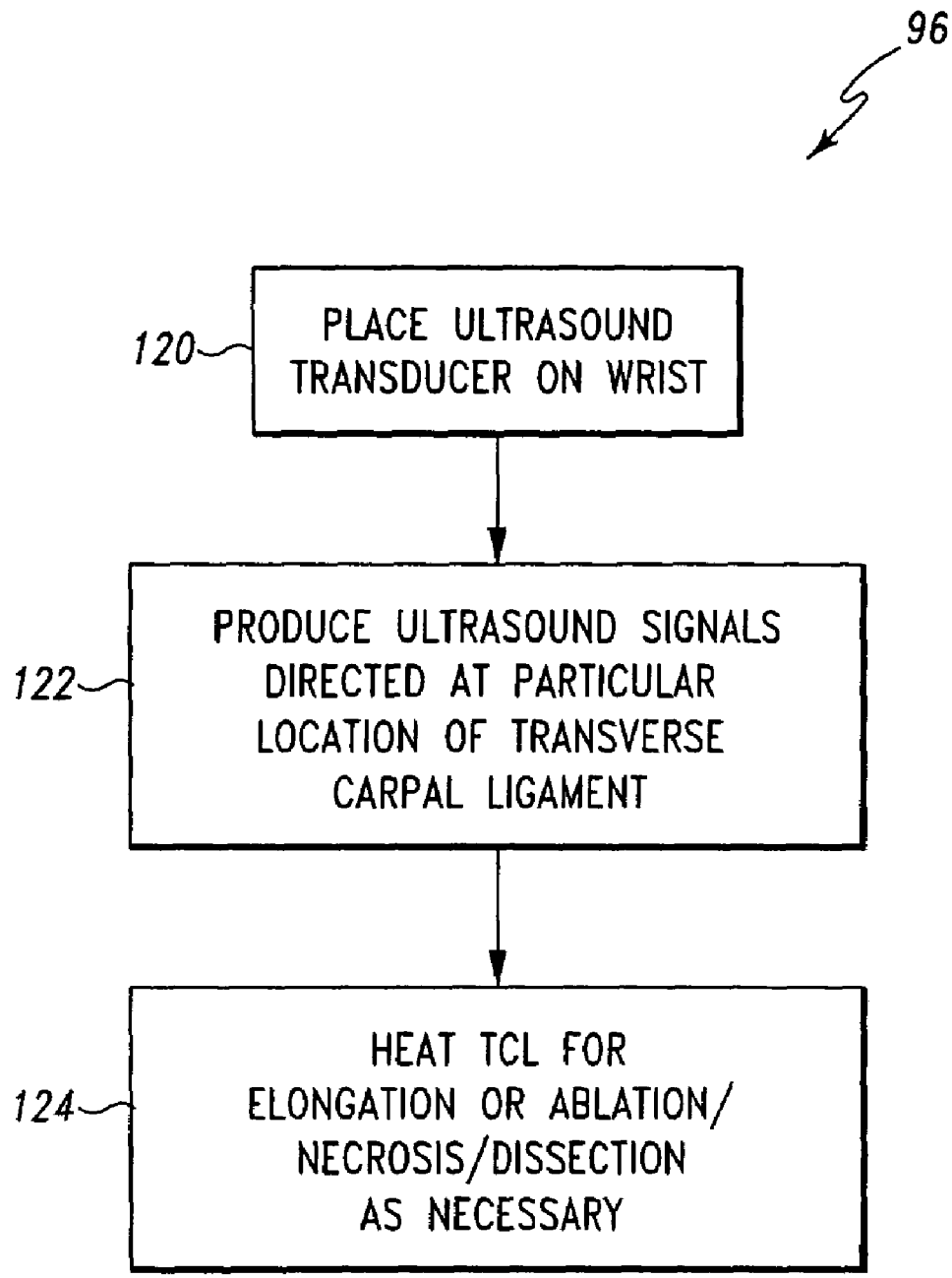
FIG. 9B is a flowchart of an exemplary manner of carrying out another step of the flowchart of FIG. 9.

In FIG. 9B, an expanded flowchart of step 96 is shown. It should be appreciated that the expanded flowchart of step 96 is only exemplary of a manner of executing step 96. In step 120, an ultrasound transducer (applicator) is strategically placed on the wrist to be imaged. In step 122, high frequency ultrasound signals are generated and directed at a particular location (target area) of the transverse carpal ligament. In step 124, the target location of the transverse carpal ligament is heated by the ultrasound signals to provide elongation, ablation, necrosis and/or dissection as appropriate.

There is a plurality of advantages of the subject invention arising from the various features of the subject invention described herein. It will be noted that further alternative embodiments of the subject invention may not include all of the features described yet still benefit from at least some of the advantages of such features. Those of ordinary skill in the art may readily devise their own implementations of the subject invention that incorporate one or more of the features of the subject invention and that fall within the sprit and scope of the subject invention.

What is claimed is:

1. A method of performing treatment on a transverse carpal ligament of a wrist of a patient comprising:
   (a) generating, during a procedure to treat a transverse carpal ligament in a patient's wrist, an image of a portion of the wrist of the patient using a first ultrasound frequency;
   (b) locating a target area on the transverse carpal ligament of the wrist of the patient relative to internal structures of the wrist proximate the transverse carpal ligament using the image generated during the procedure; and
   (c) directing a second ultrasound frequency at the transverse carnal ligament to cause a high temperature at the target area of the transverse carpal ligament to cause the target area of the transverse carpal ligament to undergo one of elongation, ablation, necrosis and dissection during the procedure,
   wherein the directing of the second ultrasound frequency at the transverse carpal ligament to cause the high temperature is performed in a non-invasive manner.

2. The method of claim 1, wherein the second ultrasound frequency is directed at the transverse carpal ligament to elongate and cause necrosis of the target area.

3. The method of claim 1, wherein locating a transverse carpal ligament of a wrist of a patient relative to internal structures of the wrist proximate the transverse carpal ligament includes generating the first ultrasound frequency with a frequency that is lower than the second ultrasound frequency that causes the high temperature.

4. The method of claim 3, wherein the first ultrasound frequency is in a range of about 1.0 MHz to about 7.5 MHz and the second ultrasound frequency is in a range of about 7.5 MHz to about 35 MHz.

5. A method of performing a medical procedure comprising:
   transmitting and receiving a first ultrasound signal directed at a wrist of a patient during a procedure to treat a transverse carpal ligament in the wrist;
   generating an image of a portion of the transverse carpal ligament in the wrist of the patient using the first ultrasound signal;
   targeting an area of the transverse carpal ligament in the wrist based upon the image generated during the procedure;
   transmitting a second ultrasound signal at the targeted area to cause a high temperature condition sufficient for irreversible treatment of structure at the targeted area of the transverse carpal ligament in the wrist with the second ultrasound signal; and
   transmitting the second ultrasound signal through skin of the patient to cause irreversible treatment of the targeted area of the transverse carpal ligament.

6. The method of claim 5, wherein transmitting the second ultrasound signal comprises:
   generating the second ultrasound signal at a frequency greater than the frequency of the first ultrasound signal.

7. A method for treating a transverse carpal ligament comprising:
   imaging a transverse carpal ligament in a patient's wrist to identify a target area of the transverse carpal ligament during a procedure to treat the transverse carpal ligament; and
   directing a first ultrasound frequency at the identified target area of the transverse carpal ligament to cause the target area to undergo one of elongation, ablation, necrosis, and dissection,
   wherein the first ultrasound frequency is directed through skin of the patient's wrist towards the transverse carpal ligament in the patient's wrist.

8. The method of claim 7, the imaging further comprising:
   transmitting a second ultrasound frequency through skin of the patient's wrist to the transverse carpal ligament; and
   generating an image of the transverse carpal ligament from reflections of the second ultrasound frequency received from the transverse carpal ligament.

9. The method of claim 8, wherein the second ultrasound frequency is transmitted at a frequency in a range of about 1.0 MHz to about 7.5 MHz.

10. The method of claim 7, wherein the first ultrasound frequency is in a range of about 7.5 MHz to about 35 MHz.

* * * * *